(12) United States Patent
Zeinali et al.

(10) Patent No.: US 7,749,438 B2
(45) Date of Patent: *Jul. 6, 2010

(54) FLUOROPHORE EMBEDDED/INCORPORATING/BRIDGED PERIODIC MESOPOROUS ORGANOSILICAS AS RECOGNITION ELEMENTS FOR OPTICAL SENSORS

(75) Inventors: Mazyar Zeinali, Columbia, MD (US); Brandy J White, Alexandria, VA (US); Paul T Charles, Bowie, MD (US); Michael A Markowitz, Springfield, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 671 days.

This patent is subject to a terminal disclaimer.

(21) Appl. No.: 11/465,343

(22) Filed: Aug. 17, 2006

(65) Prior Publication Data

US 2010/0081205 A1 Apr. 1, 2010

Related U.S. Application Data

(60) Provisional application No. 60/708,913, filed on Aug. 17, 2005.

(51) Int. Cl.
*G01N 33/00* (2006.01)

(52) U.S. Cl. .............................. 422/57; 422/50; 422/56; 422/68.1; 422/82.05; 422/82.06; 422/82.07; 422/82.08

(58) Field of Classification Search ................... 422/57, 422/50, 56, 68.1, 82.05, 82.06, 82.07, 82.08, 422/83

See application file for complete search history.

(56) References Cited

U.S. PATENT DOCUMENTS

| | | | | |
|---|---|---|---|---|
| 6,028,025 A | * | 2/2000 | Ying et al. | .................. 502/171 |
| 6,310,110 B1 | | 10/2001 | Markowitz et al. | |
| 6,583,191 B2 | | 6/2003 | Markowitz et al. | |
| 6,660,780 B2 | | 12/2003 | Markowitz et al. | |
| 6,673,246 B2 | | 1/2004 | Markowitz et al. | |
| 6,713,416 B2 | | 3/2004 | Markowitz et al. | |

OTHER PUBLICATIONS

Wahab "Periodic Mesoporous Organosilica materials incorporating various organic functional groups: Synthesis, structural characterization and morphology" Chem. Material. published Mar. 17, 2005, 17, pp. 2165-2174.*

Inagaki et al., Novel Mesoporous Materials with a Uniform Distribution of Organic Groups and Inorganic Oxide in Their Framewokrs, J. Am. Chem. Soc. 1999. 121,9611.

(Continued)

*Primary Examiner*—Sam P Siefke
(74) *Attorney, Agent, or Firm*—Amy Ressing

(57) ABSTRACT

Periodic mesoporous organosilicas (PMO) which incorporate an optically active molecule into the material for use as an optical indicator of target binding. This material combines the stability, selectivity, and high density of binding sites characteristic of the PMO with the sensitivity and selectivity of the optically active molecule. The material undergoes a change when exposed to a sample containing a target molecule. The change can be observed by visual inspection or through the use of fluorescence spectra.

18 Claims, 12 Drawing Sheets

OTHER PUBLICATIONS

Asefa et al., Periodic mesoporous organosilicas with organic groups inside the channel walls, Nature 1999. 402, 867.

Melde et al., Mesoporous Sieves with Unified Hybrid Inorganic/Organic Frameworks, Chem. Mater. 1999, 11, 3302.

Kreseg et al., Ordered mesoporous molecular sieves synthesized by a liquid-crystal template mechanism. Nature, 359. 710, Oct. 22, 1992.

Burleigh et al., Direct synthesis of periodic mesoporous organosilicas: Functional Incorporation by Co-Condensation with Organosilanes, J. Phys. Chem. B 2001, 105, 9935.

White, et al., Reagent-less detection of a competitive inhibitor of immobilized acetylcholinesterase. BiosenBioelec 2002, 17, 361.

White, et al., Enzyme-based detection of Sarin (GB) using planar waveguide absorbance spectroscopy, SensLett 2005, 3, 36.

White, et al., Competitive Inhibition of Cabonic Anhydrase by Water Soluble Porphyrins: Use of cabonic anhydrase as a CO2 Sensor, SensLett 2005, 3, 59.

Burleigh, et al, Porous Polysilsesquioxanes for the Adsorption of Phenols, Environ Sci Technol. 36 (2002) 2515.

Jayasundera et al., Organosilica Copolymers for the Adsorption and Separation of Multiple Pollutants, J. Phys. Chem. B 109, 9198-9201. 2005.

Burleigh et al., Porous Polysilsesquioxanes for the Adsorption of Phenols, Environ Sci Technol 36, 2515-18, 2002.

Alvaro et al., Photochemical modification of the surface area and tortuosity of a trans-1,2-bis(4-pyridyl)ethylene periodic mesoporous MCM organosilica, Chem. Commun, 2012-13, 2002.

Mal et al., Photocontrolled reversible release of guest molecules from coumarin-modified mesoporous silica, Nature 421, 350-3, 2003.

Malinski, The Porphyrin Handbook, K. M. Kadish, K. M. Smith and R. Guilard, (Eds.). vol. 6, pp. 231. Academic Press, New York, 2000.

Mauzerall, Spectra of molecular complexes of porphyrins in aqueous solution, Biochemistry 4, 1801-1810, 1965.

Rakow and Suslick, A colorimetric sensor array for odour visualization, Nature 406, 710-713, 2000.

Schneider and Wang, Ligand-Porphyrin Complexes: Quantitative Evaluation of Stacking and Ionic Contributions, J. Org. Chem 59, 7464-7472, 1994.

Shelnutt, Molecular complexes of copper uroporphyrin with aromatic acceptors, J. Phys. Chem 87, 605-616, 1983.

Umar et al., Self-assembled monolayer of copper(II) meso-tetra(4-sulfanatophenyl) porphyrin as an optical gas sensor, Sensors and Actuators B 101, 231-235, 2004.

Montmeat et al., Metalloporphyrins as sensing material for quartz-crystal microbalance nitroaromatics sensors, 2005.

Ni et al., An anthracene/porphyrin dimer fluorescence energy transfer sensing system for picric acid .63, 2. 251-257, 2004.

Takezaki and Tominaga, Fluorescence quenching reaction of porphyrins in micelles : Ionic porphyrins quenched by nitrobenzene in ionic micelles, J. Photochem. Photobiol. A 174, 113-118, 2005.

Shea and Loy, Bridged Polysilsesquioxanes Molecular Engineered Hybrid Organic-Inorganic Materials, Chem. Mater. 13, 3306-3319, 2001.

Awawdeh et al., Solid-state optical detection of amino acids, Sensors and Actuators B-Chemical 91, 227-230, 2003.

Kibbey and Meyerhoff, Preparation and characterization of covalently bound tetraphenylporphyrin-silica gel stationary phases for reversed-phase and anion-exchange chromatography, Analytical Chemistry 65, 2189-2196, 1993.

White and Harmon, Interaction dipicolinic acid with water-soluble and immobilized porphyrins, Sensors and Actuators B 97, 277-83, 2004.

Connors, Binding Constants: The Measurement of Molecular Complex Stability, John Wiley & Sons, New York, 1987.

White and Harmon, Optical Determination of Bacterial Exosporium Sugars Using Immobilized Porphyrins, IEEE Sensors Journal 5, 726-732, 2005.

* cited by examiner

|  | SAMPLE | IMAGES | RGB VALUES | IDEALIZED IMAGES | DIFFERENCE IMAGES | RGB VALUES |
|---|---|---|---|---|---|---|
| VAPOR PHASE SAMPLES | PMO WITH ETHANOL | | R 251 | | | |
| | | | G 231 | | | |
| | | | B 226 | | | |
| | PMO WITH CYCLOHEXANE | | R 228 | | | R 232 |
| | | | G 209 | | | G 233 |
| | | | B 196 | | | B 225 |
| | PMO WITH TOLUENE | | R 243 | | | R 247 |
| | | | G 231 | | | G 255 |
| | | | B 223 | | | B 252 |
| LIQUID PHASE SAMPLES | PMO WITH ETHANOL | | R 232 | | | |
| | | | G 220 | | | |
| | | | B 215 | | | |
| | PMO WITH CYCLOHEXANE | | R 209 | | | R 232 |
| | | | G 196 | | | G 231 |
| | | | B 163 | | | B 230 |
| | PMO WITH TOLUENE | | R 154 | | | R 177 |
| | | | G 140 | | | G 175 |
| | | | B 115 | | | B 155 |

FIG. 6

FLUOROPHORE EMBEDDED/INCORPORATING/BRIDGED PERIODIC MESOPOROUS ORGANOSILICAS AS RECOGNITION ELEMENTS FOR OPTICAL SENSORS

CROSS-REFERENCE TO RELATED APPLICATIONS

This Application is a Non-Prov of Prov (35 USC 119(e)) application 60/708,913 filed on Aug. 17, 2005. This application is related to N.C. 97,346, filed concurrent herewith, based on Prov (35 USC 119(e)) application 60/708,912, both incorporated herein in full by reference.

BACKGROUND OF THE INVENTION

Due to recent events world wide, there is a high level of interest in the detection of low level concentrations of explosives such as TNT (2,4,6-trinitrotoluene) and RDX (cyclotrimethylenetrinitramine) for the identification of individuals and areas exposed to these compounds. Detection of these compounds is also of interest for monitoring levels in soil and ground water near sites of munitions handling and storage. Several U.S. Department of Defense (DoD) and former DoD munitions handling sites have elevated concentrations of explosives and/or volatile organic compounds (VOCs) in soil and groundwater (U.S. Army Environmental Center, Remediation of explosives contaminated soil, http://aec.army.mil/usaec/technology/cleanup01.html 2003; Crockett et al. *Field sampling and well selecting on-site analytical methods for explosives in water,*" Rep. No. 600/S-99/002. *U.S. Environmental Protection Agency,* 1999). VOCs are also found in a wide range of consumer products including paints and cleaning supplies and are produced by chemical manufacturing processes, automotive exhaust, and the evaporation of petroleum-based products (U.S. Environmental Protection Agency, USEPA, U.S. Consumer Product Safety Commission. 1995. *The Inside Story: A Guide to Indoor Air Quality. U.S. Environmental Protection Agency Document* #402-K-93-007, 1995). Exposure to TNT or RDX can result in skin, eye, and respiratory tract irritation; nervous system irregularities; and convulsions. Exposure to high levels of VOCs can result in irritation of mucous membranes, headaches, nausea, damage to liver or kidneys, and is suspected of increasing the risk of certain types of cancer (USEPA, 1995).

Dogs are currently the choice for sensitive, broad-spectrum detection of explosives (Haupt et al., *Applicability of Portable Explosive Detection Devices in Transit Environments,"* Rep. No. 86. Transportation Research Board of the National Academies., Washington, D.C., 2004). They are capable of detection of a wide range of analytes including explosives, fuels, and even bio-threats at exceptionally low levels: they are resistant to masking interferents; and they are able to spatially locate the source. Dogs also provide additional security in the form of a deterrent. Unfortunately, dogs fatigue after working for short periods of time and their training and upkeep is expensive requiring a dedicated handler. Ion mobility spectrometry is based on the time required for various ions of a vaporized and ionized sample to reach the detector (Fetterolf and Clark, *Detection Of Trace Explosive Evidence By Ion Mobility Spectrometry, Journal of Forensic Sciences* 38, 28-39, 1993; Garofolo et al., *Rapid Communications in Mass Spectrometry* 8, 527-532, 1994; Koyuncu et al., *Turkish Journal of Chemistry* 29, 255-264, 2005; Pen et al., *Solid phase microextraction ion mobility spectrometer interface for explosive and taggant detection, Journal of Separation Science* 28, 177-183, 2005). Ion mobility spectrometry lends itself to the development of portable instruments as it is sensitive and does not require ionization under vacuum. Limitations include false alarms due to similar drift times of non-threat agents and lack of quantitative capability. Electron capture detection is similar to ion mobility spectrometry (Baffle et al., *Enhanced Detection of Nitroaromatic Explosive Vapors Combining Solid-phase Extraction-Air Sampling, Supercritical Fluid Extraction and Large Volume Injection-GC, Analytical Chemistry* 75, 3137-3144, 2003; Monteil-Rivera et al., *Use of solid-phase microextraction/gas chromatography—electron capture detection for the determination of energetic chemicals in marine samples, Journal of Chromatography A* 1066, 177-187, 2005; Zhang et al., *Use of pressurized liquid extraction (PLE)/gas chromatography-electron capture detection (GC-ECD) for the determination of biodegradation intermediates on hexahydro*-1,3,5-*trinitro*-1,3,5-*triazine (RDX) in soils, Journal of Chromatography B-Analytical Technologies in the Biomedical and Life Sciences* 824, 277-282, 2005). These detectors measure the affinity of the sample for electrons. False positive rates are reported to be higher than those of ion mobility spectrometry (Haupt et al., 2004); individual explosives cannot be identified by electron capture detection; and compressed gases such as Helium or Argon are required. High performance liquid chromatography and mass spectrometry are well established, high sensitivity techniques for the detection of explosives, but are suitable for use in laboratory settings primarily.

There are several new technologies being developed for explosives detection: surface acoustic wave (Grate, *Wave Microsensor Arrays for Vapor Sensing, Chemical Reviews* 100, 2627-2647, 2000; Houser et al., *Rational materials design of sorbent coatings for explosives: applications with chemical sensors, Talanta* 54, 469-485, 2001; Kannan et al., *Detection of Landmine Signature using SAW-based Polymer-coated Chemical Sensor, Defense Science Journal* 54, 309-315, 2004), semiconducting organic polymers, and amplifying fluorescent polymers. Detection by surface acoustic wave sensors is based on a change in frequency which corresponds to a change in mass caused by adsorption of target analyte by a polymer surface. Surface acoustic wave sensors can employ an array of polymers allowing discrimination of a range of analytes as well as providing reduction of false positives. These sensors are somewhat sensitive to temperature fluctuations and tend to be humidity sensitive. Polymer surfaces are regenerable. Semi-conducting organic polymers provide highly sensitive detection of electron deficient nitroaromatics such as TNT (Rose et al., *Sensitivity gain in chemosensing by lasing action in organic polymers, Nature* 434, 876-879, 2005). Detection is based on quenching of polymer fluorescence upon analyte binding. Exceptional detection limits under ambient conditions have been reported, however, pulsed laser excitation is required and the polymers are subject to photo-bleaching. The technique is limited to $NO_2$-containing compounds and is subject to interference by non-threat compounds of similar structure. Amplifying fluorescent polymers use a molecular-wire with multiple binding sites and multiple fluorophores (Cumming et al., *Using Novel Fluorescent Polymers as Sensory Materials for Above-Ground Sensing of Chemical Signature Compounds Emanating from Buried Landmines, IEEE Transactions on Geoscience and Remote Sensing* 39, 1119-1128, 2001). Interaction of a target molecule with a single binding site results in quenching of many fluorophores providing an amplifying effect. Laser excitation is not necessary. TNT and compounds of similar structure such as dinitrotoluene can be detected, though without discrimination. Detection is accomplished in real-time and polymers are regenerable/reusable. Other types of detection techniques employ proteins such as antibodies and enzymes for the specific recognition of target molecules.

PMOs are organic-inorganic polymers with highly ordered pore networks and large internal surface areas. They were first reported in 1999 (Inagaki et al. *Mesoporous Materials with a Uniform Distribution of Organic Groups and Inorganic Oxide in Their Frameworks*, J. Am. Chem. Soc. 1999, 121, 9611; Asef et al., *Periodic mesoporous organosilicas with organic groups inside the channel walls*, Nature 1999, 402, 867; Melde et al., *Mesoporous Sieves with Unified Hybrid Inorganic/Organic Frameworks*, Chem. Mater. 1999, 11, 3302), these organosilicas were synthesized using a surfactant template approach (Kreseg et al., *Ordered mesoporous molecular sieves synthesized by a liquid-crystal template mechanism, Nature*, 359, 710, 22 Oct. 1992, Burleigh et al., *Direct synthesis of periodic mesoporous organosilicas: Functional Incorporation by Co-Condensation with Organosilanes*, J. Phys. Chem. B 2001, 105, 9935) and have narrow pore size distributions with few blocked pores or obstructions commonly found in amorphous materials to impede molecular diffusion throughout their pore networks. PMOs possess structural rigidity arising from the siloxane groups and functionality due to the organic bridging group. In addition, specificity can be imparted to the PMOs via a template directed molecular imprinting process. Due to their structural stability, functionality, and specificity, the PMOs are very efficient sorbents for the removal, sequestration, and preconcentration of pollutants and/or any targeted compound from both vapor and aqueous phase. Yet a secondary means, such as a spectroscopic or electrochemical technique, is required for the specific detection of the sorbate. The addition/embedding of molecules (ie fluorophores) would in effect add a sensing capability to PMOs through the spectrophotometric response of the embedded molecule to changes in its surrounding environment.

PMOs are hybrid materials containing organic functionality in a silica matrix through covalent silica-carbon bonds which serve as an "organic bridge" within the wall of the matrix. These materials possess relatively high surface areas with high organic loading which can be modified by incorporating different organic bridging materials or multiple organic groups (Jayasundera et al., *Organosilica Copolymers for the Adsorption and Separation of Multiple Pollutants*, J. Phys. Chem. B 109, 9198-9201, 2005). The structure of the material provides a high internal surface area as well as narrow pore size distribution. Template directed molecular imprinting, the use of a target-like compound, can be used to produce more homogeneous pore size and distribution as well as to further enhance binding characteristics and selectivity. PMO materials have been described for use in environmental clean-up for the adsorption of toxic chemicals from water sources (Burleigh et al., *Porous Polysilsesquioxanes for the Adsorption of Phenols*, Environ Sci Technol 36, 2515-18, 2002) and, with photochemical modification, for potential use in switches and sensors (Alvaro et al., *Photochemical modification of the surface area and tortuosity of a trans-1, 2-bis(4-pyridyl)ethylene periodic mesoporous MCM organosilica*, Chem. Commun, 2012-13, 2002; Mal et al., *Photocontrolled reversible release of guest molecules from coumarin-modified mesoporous silica*, Nature 421, 350-3, 2003). The PMOs can be optimized for adsorption of TNT and similar compounds, however, PMO materials can be synthesized for adsorption of many materials, including, but not limited to, chemical warfare agents, pesticides, volatile organic compounds, or toxic industrial products. Optimization of the PMO materials is disclosed in Markowitz, et al., U.S. patent application Ser. No. 11/307,286, filed Jan. 31, 2006, incorporated herein in full by reference. The use of periodic mesoporous organosilicas (PMOs) as recognition elements offers advantages in stability, selectivity, and ease of modification.

The molecular structure of the porphyrin consists of a large macrocycle around which a minimum of 22 $\pi$-electrons are shared, resulting in a high degree of sensitivity to the immediate environment of the molecule. This large number of $\pi$-electrons results in a large extinction coefficient and spectral characteristics that are highly sensitive to changes in the environment of the molecule. In general, porphyrins possess a strong absorption band around 400 nm with an extinction coefficient that can exceed 500 mM-1·cm-1 as well as several less intense bands between 450 and 700 nm. Porphyrins are typically intensely fluorescent with emission bands between 600 and 750 nm. Porphyrins have been used in a wide range of optical detection applications (Malinski, *The Porphyrin Handbook*, K. M. Kadish, K. M. Smith and R. Guilard, (Eds.). Vol. 6, pp. 231. Academic Press, New York, 2000) and the sensitivity of porphyrin spectrophotometric characteristics to the presence of cyclic organics has been demonstrated by several groups (Mauzerall, *Spectra of molecular complexes of porphyrins in aqueous solution*, Biochemistry 4, 1801-1810, 1965; Rakow and Suslick, *A colorimetric sensor array for odour visualization*, Nature 406, 710-713, 2000; Schneider and Wang, *Ligand-Porphyrin Complexes: Quantitative Evaluation of Stacking and Ionic Contributions*, J. Org. Chem 59, 7464-7472, 1994; Shelnutt, *Molecular complexes of copper uroporphyrin with aromatic acceptors*, J. Phys. Chem 87, 605-616, 1983; Umar et al., *Self-assembled monolayer of copper(II) meso-tetra(4-sulfanatophenyl) porphyrin as an optical gas sensor*, Sensors and Actuators B 101, 231-235, 2004).

The changes in spectral characteristics of the porphyrin are specific for interaction with different molecules allowing for discrimination of analytes even within closely related structures such as amino acids of differing chirality. Because of these unique characteristics, porphyrins are used in a wide variety of sensor applications for the detection of analytes ranging from metal ions and volatile organic compounds to proteins. Recently arrays of different porphyrins have incorporated in fluorescence-based electronic noses. Recent work (White, et al., *Reagent-less detection of a competitive inhibitor of immobilized acetylcholinesterase*, BiosenBioelec 2002, 17, 361) has shown that porphyrins can be used in conjunction with enzymes to achieve a higher degree of selectivity and allow for specific detection within a class of compounds only. The reversible, competitive inhibition of an enzyme by a porphyrin has been used for the detection both in solution and vapor phase of analytes such as organophosphates (including nerve agents/stimulants) and carbon dioxide (White, et al., *Enzyme-based detection of Sarin (GB) using planar waveguide absorbance spectroscopy*, SensLett 2005, 3, 36 and White, et al., *Competitive Inhibition of Carbonic Anhydrase by Water Soluble Porphyrins: Use of carbonic anhydrase as a $CO_2$ Sensor*, SensLett 2005, 3, 59). Porphyrins have been previously used in a detection scheme using a flat-bed scanner (Rakow and Suslick, *A colorimetric sensor array for odour visualization*, Nature 406, 710-713, 2000), however the porphyrins were immobilized in gel, which leads to a lower degree of selectivity than porphyrins embedded in a PMO material.

One object of the present invention is to provide for a detection scheme that utilizes both the exceptional surface area and selectivity of the PMOs as well as the spectrophotometric characteristics of a fluorophore, i.e. a porphyrin, that allows rapid, specific detection of volatile organic compounds in aqueous solution and in vapor phase. Another object is to provide a detection scheme where the spectrophotometric responses of the materials to various organics at high concentrations are discernable by visual inspection of the imprinted material as well as by standard spectrophotometric techniques. A further object is to provide a material that is capable of detection/discrimination of nitroenergetics and closely related compounds in aqueous solution. These and other objects are provided by the invention disclosed.

BRIEF SUMMARY OF THE INVENTION

The PMO material disclosed herein is capable of detecting the presence of aromatic compounds with specificity owing both to the formation of the molecular imprint of the organosilicate bridged PMO imprint and the sensitivity of the fluorophore spectral characteristics. Detection is possible using fluorescence emission spectra or by visual inspection. The imprinted porphyrin embedded PMO is a high capacity, selective sorbent with the potential for use as a recognition element. The imprinted porphyrin embedded PMO provides a tool to address the wide range of current and future chemical sensor and monitoring needs with the potential for stand-off-point detection systems. The material has potential for use as a recognition element that is more robust than the proteins currently used in many systems in addition to offering response times on the order of minutes.

BRIEF DESCRIPTION OF THE DRAWINGS

FIG. 6 shows that the changes in the porphyrin spectrophotometric characteristics;

DETAILED DESCRIPTION OF THE INVENTION

The incorporation of the porphyrin into the nanoporous organosilicas is described, as well as the use of the material for detecting an analyte. The nanoporous organosilicas provide a degree of selectivity allowing for detection within a class of compounds in this case aromatics. The porphyrin provides a spectrophotometric response to the change in the environment within the imprint. This spectrophotmetric response allows for visual detection of the analyte. The PMO alone provides no direct spectral response to the presence of an analyte and therefore cannot be used as a detector/sensor. The porphyrin alone responds to the presence of any change in its immediate surroundings and therefore requires extensive spectral deconvolution when used as a sensor. Additionally, decontamination applications involving the PMO materials alone are based on adsorption of the contaminant onto the silicate and not on degradation of the contaminant. The porphyrin imprinted PMO material described herein is capable of catalyzing the degradation of the analyte using sunlight, allowing for use of the imprinted PMO material for repeated detection/decontamination applications.

Combining the periodic mesoporous organosilica (PMOs) with the porphyrin achieves a semi-selective sensing element for the optical detection of cyclic organics and a material to catalyze the conversion of nitroaromatics when placed under sunlight illumination.

Photocatalyzed degradation to mineral of potentially harmful aromatics is possible using sunlight or other excitation source covering the blue to red regions of the visible spectrum owing to the ability of the nanoporous organosilicas to facilitate proper orientation of the fluorophore and analyte and to the capacity of porphyrins to catalyze reactions upon photo-excitation. Template directed molecular imprinted materials and processes that yield selective and higher capacity nanoporous organosilicas and their regeneration capability are disclosed in Markowitz et. al., U.S. Pat. No. 6,310,110, issued Oct. 30, 2001, Markowitz et. al., U.S. Pat. No. 6,583,191, issued Jun. 24, 2003, Markowitz et. al., U.S. Pat. No. 6,660,780, issued Dec. 9, 2003, Markowitz et. al., U.S. Pat. No. 6,673,246, issued Jan. 6, 2004, and Markowitz et. al., U.S. Pat. No. 6,713,416, issued Mar. 30, 2004, all incorporated herein by reference.

Figure 1:
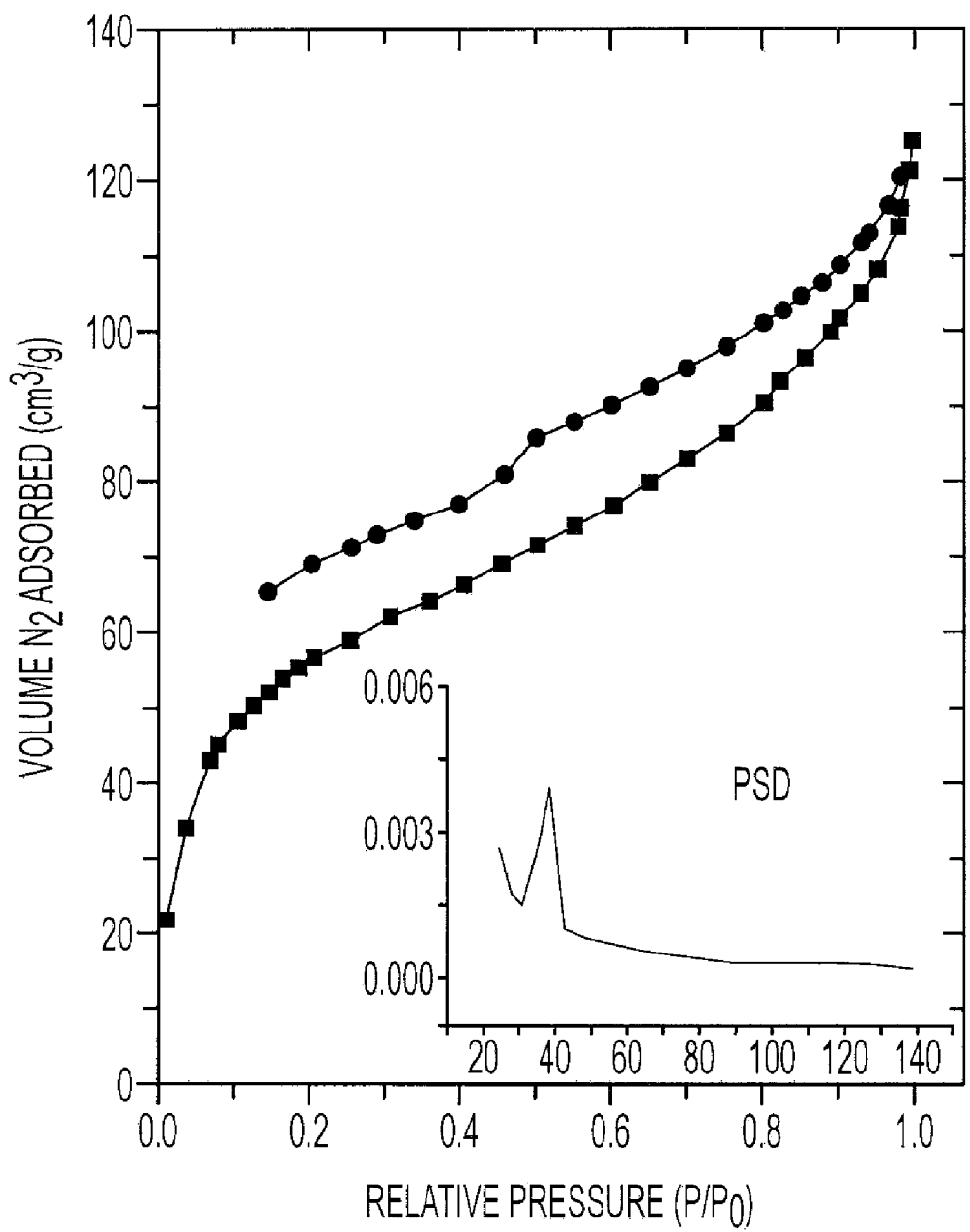
FIG. 1 shows nitrogen sorption/desorption isotherms.

Synthesis of porphyrin embedded molecularly imprinted PMO. The physiochemical properties of the material is listed in Table 1. FIG. 1 shows the nitrogen sorption (■) and desorption (●) isotherms for IPDEB PMOs. The porphyrin embedded PMO maintains porosity and with slight reduction in surface area. The porphyrin was chosen as a result of the minimal challenges presented during synthesis of the PMO materials. Other fluorophores/porphyrins can be used that are optimized for nitroenergetics detection (Montmeat et al. *Metalloporphyrins as sensing material for quartz-crystal microbalance nitroaromatics sensors,* 2005; Ni et al., *An anthracene/porphyrin dimer fluorescence energy transfer sensing system for picric acid,* 63, 2, 251-257, 2004; Takezaki and Tominaga, *Fluorescence quenching reaction of porphyrins in micelles: Ionic porphyrins quenched by nitrobenzene in ionic micelles,* J. Photochem. Photobiol. A 174, 113-118, 2005). PMO structures have been demonstrated for adsorption of nitroaromatics previously (Burleigh et al., *Environ Sci Technol* 36, 2515-18, 2002), however they did not incorporate the porphyrin, a large organic molecule, into the structure. This incorporation causes a number of changes in material properties. Those skilled in the art would understand that other materials can be created by the use of different bridging molecules and surfactants or alternate methods of porphyrin inclusion (Shea and Loy, *Bridged Polysilsesquioxanes Molecular Engineered Hybrid Organic-Inorganic Materials,* Chem. Mater. 13, 3306-3319, 2001).

TABLE 1

Physiochemical properties of synthesized PMOs.

| PMO | BET surface area ($m^2$/g) | Total Pore Volume ($cm^3$/g) | BJH Pore Diameter (Å) |
|---|---|---|---|
| IDEB | 244 | 0.19 | 31 |
| IPDEB | 209 | 0.18 | 34 |

Figure 2A:
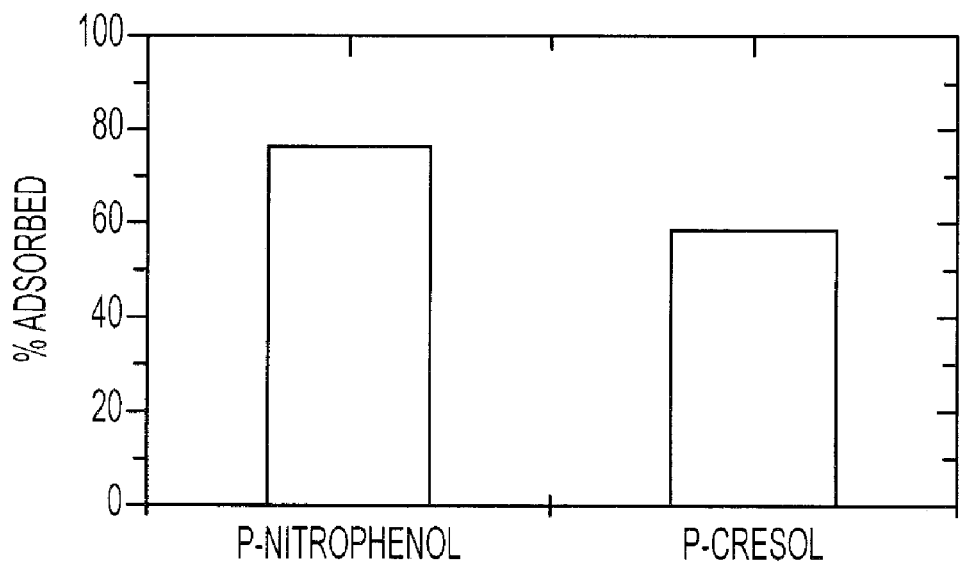
FIG. 2 shows the adsorption of p-nitrophenol and p-cresol from single sorbate and competitive binary solutions.
Figure 2B:
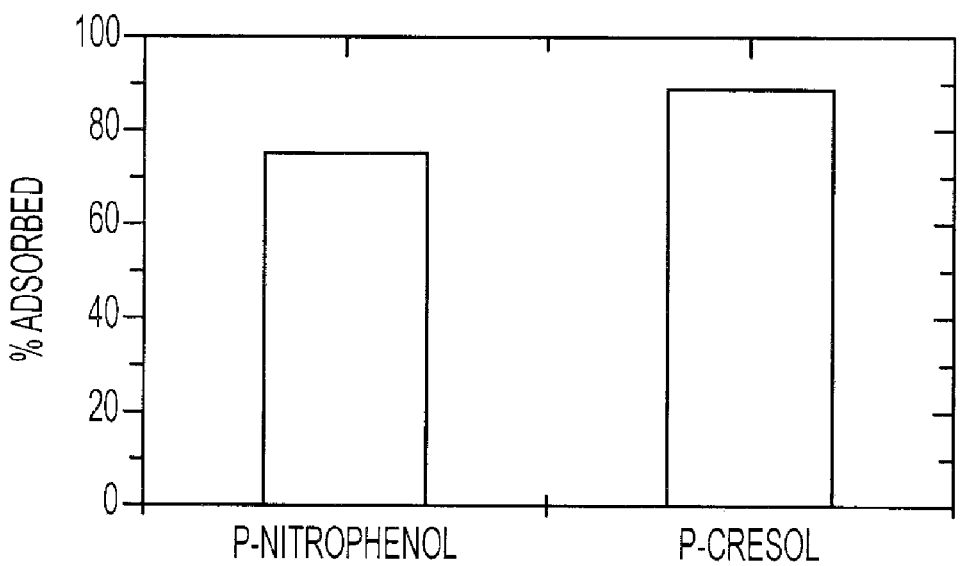

Adsorption of phenols onto porphyrin embedded molecularly imprinted PMO. The adsorption of p-nitrophenol and p-cresol from single sorbate and competitive binary solutions is shown in FIG. 2. As illustrated, the IPDEB PMO shows high affinity for substituted phenols from single sorbate (see FIG. 2A) and binary (see FIG. 2B); competitive p-nitrophenol-p-cresol) solution.

Figure 3A:
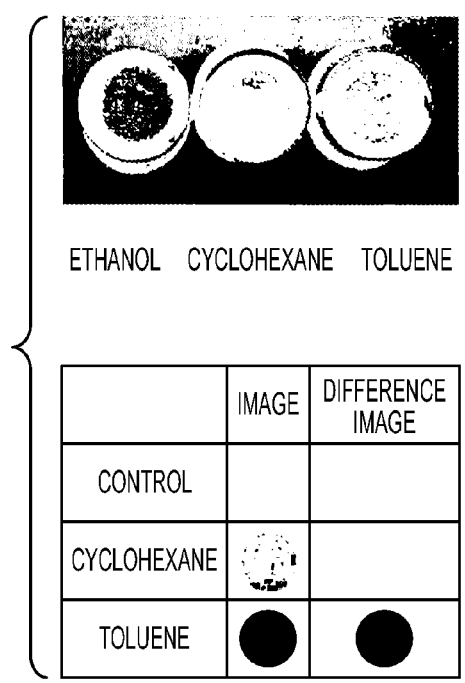
FIG. 3 shows the IPDEB sensing capability in a solution environment.
Figure 3B:
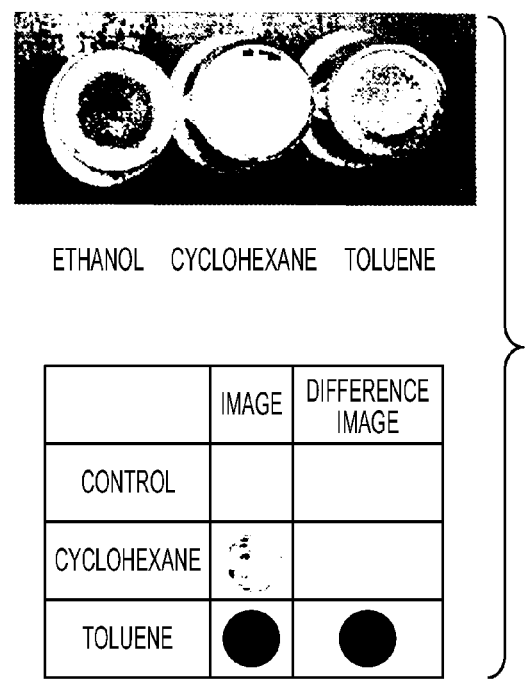
Figure 4:
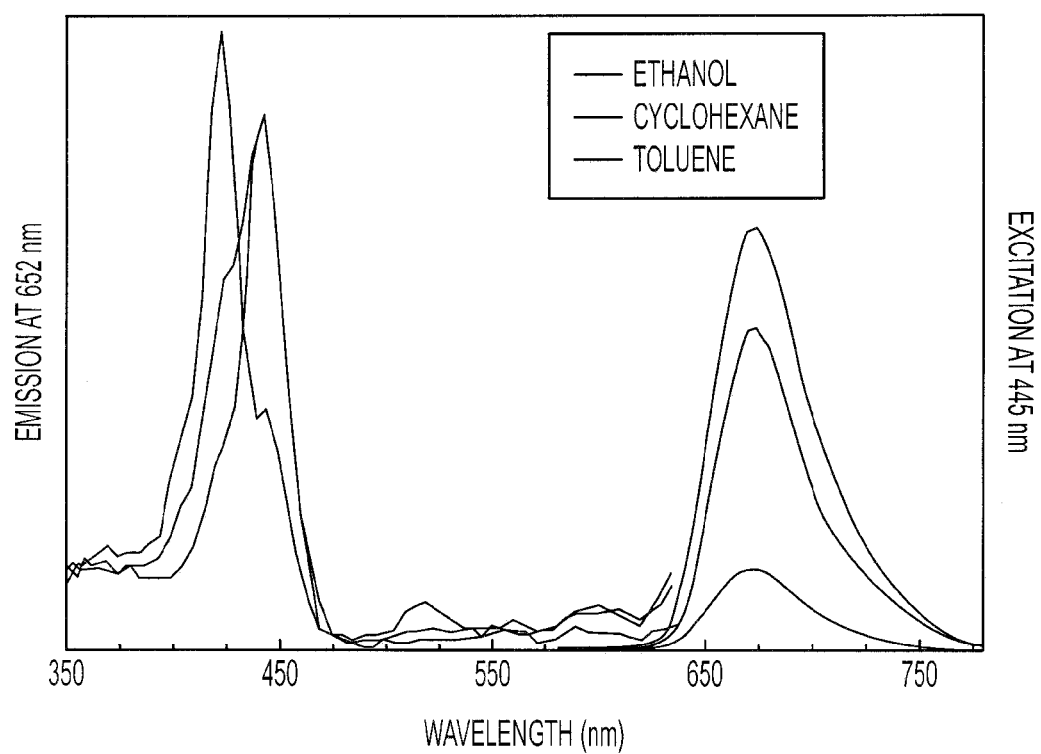
FIG. 4 shows the fluorescence excitation and emission spectra of samples described in FIG. 3B.

Sensor/detection capability of porphyrin embedded molecularly imprinted PMO. FIG. 3 shows the IPDEB sensing capability in a solution environment. The IPDEB PMO was exposed to liquid solvent and the resulting change in the powder color recorded via color digital flat-bed scanner. This figure clearly illustrates the changes in the spectrophotometric characteristics of the porphyrin embedded PMO resulting from changes in its environment. In addition, the spectrophotometric response of the material to analyte presence can be monitored via fluorescence spectroscopy. FIG. 3 shows the colorimetric response of IPDEB to solvents under (A) neutral and (B) acidic conditions. Also shown are the results of difference image calculation using Adobe PhotoShop. Difference images are calculated based on the RGB values for the scanned images. FIG. 4 shows the fluorescence excitation and emission spectra of samples described in FIG. 3B.

Figure 5:
FIG. 5 shows the IPDEB sensing capability in a vapor environment.

FIG. 5 shows the IPDEB sensing capability in a vapor environment. The IPDEB PMO was exposed to solvent vapor and the resulting change in the powder color recorded via color digital flat-bed scanner. This figure clearly illustrates the spectrophotometric changes resulting from the interaction of the porphyrin embedded PMO with the vapors.

Having described the invention, the following example is given as a particular embodiment thereof and to demonstrate the practice and advantages thereof. It is understood that the examples are given by way of illustration and are not intended to limit the specification or the claims in any manner.

Meso-tetra(4-carboxyphenyl) porphine (CTPP) was obtained from Frontier Scientific, Logan. UT and used as received. 1,4-bis(trimethoxysilylethyl)benzene was obtained from Gelest, Inc., Tullytown. Brij®76, NaOH, HCl, ethanol, p-cresol, p-nitrophenol, decylamine, and diethyl ether were purchased from Sigma-Aldrich (St. Louis, Mo.). 2,4,6-Trinitrobenzene sulfonic acid (5% w/v in methanol) was purchased from Pierce Chemical Co (Rockford, Ill.).

The template imprint molecule, decylamine trinitrobenzene (DATNB) was synthesized. The molecular structure of DATNB consists of a 10-carbon chain (decane) bound to the amino group of 1-amino 2,4,6-trinitrobenzene. Decylamine (3.4 g, 21.6 mmol) was added slowly to a stirred solution of 2,4,6-trinitrobenzenesulfonic acid in 100 mL methanol (5% w/v, 21.6 mmol). The resulting orange solution was stirred overnight and concentrated to a slurry by evaporation under reduced pressure. The crude slurry was extracted successively with 3×10 mL of 1.0 N HCl, deionized water, and 0.1 M NaOH. The remaining solid powder was dissolved in hot diethyl ether and kept at −4° C. The resulting bright yellow crystals that formed were collected by vacuum filtration, washed with cold diethyl ether, and dried under vacuum to give 7.1 g (89% yield) of the desired product. $^1$H NMR (400 MHz, CDCl$_3$, δ): 0.86 (3H, t), 1.33 (14H, m), 1.70 (2H, m), 3.07 (2H, m), 8.98 (1H, m), 9.01 (2H, s). M.p. 61.4-62.0 C. Template directed molecular imprinted materials and processes that yield selective and higher capacity nanoporous organosilicas and their regeneration capability are disclosed in Markowitz et. al. U.S. Pat. No. 6,310,110, issued Oct. 30, 2001. Markowitz et. al. U.S. Pat. No. 6,583,191, issued Jun. 24, 2003, Markowitz et. al., U.S. Pat. No. 6,660,780, issued Dec. 9, 2003, Markowitz et. al., U.S. Pat. No. 6,673,246, issued Jan. 6, 2004, and Markowitz et. al., U.S. Pat. No. 6,713,416, issued Mar. 30, 2004, all incorporated herein by reference.

Two different porphyrin-embedded diethylbenzene-bridged periodic mesoporous organosilicas (PMOs) were prepared, an imprinted (PMO-B) and a non-imprinted (PMO-A) version of the same PMO. The preparation method for the non-imprinted PMOs using Brij®76 surfactant in acidic media is described in Burleigh et al., 2002. Briefly, the Brij®76 surfactant (8.0 g) was added to 400 mL acidified water (2.42±0.05% HCl) while stirring. The covered mixture was maintained at 50° C. for 12 h prior to the addition of precursor, template imprint molecule, or porphyrin. The porphyrin was added to the covered mixture and stirred at 50° C. for an additional 3 h prior to the addition of precursor (powder used for VOC detection) or the porphyrin was added simultaneously with the precursor (for substituted phenols and nitroenergetics detection). The imprinted PMO's were prepared in a similar fashion with the addition of the template imprint molecule (0.5 g/400 mL) after surfactant equilibration followed by an additional 6 h of equilibration at 50° C. with stirring. The solution containing the surfactant and the imprint molecule was filtered through 0.2 mm filter to remove excess imprint molecule. The filtered solution was returned to 50° C. and stirred for an additional 3 h prior to the addition of the organosilane precursor. Aging, surfactant template removal, and drying were the same for both non-imprinted and imprinted PMO's and have been described in our previous publication with the exception that these powders were not refluxed in deionized water prior to surfactant removal. Physiochemical properties were characterized via gas sorption using nitrogen gas as the adsorbate at 77 K with a Micromeritics ASAP 2010 (Norcross, Ga.). The non-imprinted porphyrin-embedded PMO has BET surface area of 157 g/m$^2$, total pore volume 0.217 cm$^3$/g, and pore size of 48 Å. The porphyrin-embedded PMO material synthesized by template-directed molecular imprinting has BET surface area of 144 g/m$^2$, total pore volume 0.221 cm$^3$/g, and pore size of 54 Å.

Fluorescence emission spectra of the porphyrins in aqueous solution (excitation at 400 nm, 5 nm band width; 50 mM sodium phosphate buffer) and the porphyrin-embedded PMOs (excitation at 400 or 420 nm, 5 nm band width; water containing less than 3.65% acetonitrile) were collected in 96-well format with a Tecan XSafire monochromator-based microplate reader from 550 to 800 nm at 3 nm resolution (2.5 nm band width). Fluorescence excitation spectra were collected for emission at 652 nm (5 nm band width) from 350 nm to 650 nm at 3 nm resolution (2.5 nm band width). Absorbance spectra of porphyrins in aqueous solution were collected using the plate reader from 370 nm to 770 nm at 2 nm resolution. Difference spectra are calculated as the point-by-point subtraction of the pre-exposure spectrum from the post-exposure spectrum. Concentration dependence data presented is based on the average of measurements conducted in triplicate.

Images of the imprinted powders presented were collected using a Hewlett Packard C7670A Scan Jet flat bed scanner. Red, green, and blue (RGB) color values were determined and difference images generated using Adobe Photoshop (v 7.0). The vapor phase samples presented here were obtained by suspending the PMO material above a liquid sample of the indicated solvent. Ethanol was used as a baseline for comparison because it was the solvent used in the extraction process during synthesis. RGB values were generated based on the average across the image of the PMO material. Difference images were calculated as the vector subtraction of the ethanol RGB values from the sample RGB values.

Solution concentrations were measured using Environmental Protection Agency (EPA) method 8330 using a Waters High Performance Liquid Chromatography (HPLC) system with dual 510 pumps, a 717 autosampler coupled to a photodiode array detector. The stationary phase was an 250 mm Altech Altiima C18 column with an isocratic 50:50 methanol:water mobile phase. Amount adsorbed was calculated via difference method.

The spectrophotometric characteristics of meso-tetra(4-carboxyphenyl) porphine (CTPP) were investigated to determine the sensitivity and selectivity of the porphyrin to the presence of the organic compounds of interest. The absorbance spectrum of CTPP in sodium phosphate buffer (50 mM pH 7) has absorbance bands at 516, 565, 650, and 750 nm with extinction coefficients on the order of 30 $mM^{-1} \cdot cm^{-1}$ whereas the Soret band at 414 nm has an extinction coefficient of 515 $mM^{-1} \cdot cm^{-1}$, making the changes in this region of the spectrum much more significant. Due to these considerations, this work deals only with the changes in the Soret region of the spectrum. The absorbance difference spectra resulting from exposure of the porphyrin to p-cresol, 2,4,6-trinitrotoluene (TNT), and p-nitrophenol (50 mM sodium phosphate pH 7) were calculated as CTPP (1.5 mM)+analyte (4.5 mM) minus CTPP (data not shown). Interaction of the porphyrin with each of the compounds investigated resulted in unique changes in the absorbance spectrum. Interaction of CTPP with p-nitrophenol yields only a trough in the difference spectrum at 416 nm while interaction with p-cresol yields a peak/trough pair at 409/420 nm. A peak/trough pair in the difference spectrum at 415/422 nm results from exposure of CTPP to TNT. When excited at 400 nm, the fluorescence emission spectrum of CTPP is sensitive to TNT with increasing concentrations yielding increasing difference intensities. When plotted as peak intensity (645 nm) minus trough intensity (675 nm), the changes in the fluorescence characteristics of CTPP upon exposure to the various compounds showed half-hyperbolic dependence on concentration as expected (Connors, 1987; White and Harmon, 2004).

PMO detection of cyclic organic compounds: Porphyrin-embedded PMO material was saturated with toluene and cyclohexane. FIG. 6 shows that the changes in the porphyrin spectrophotometric characteristics for the two analytes are distinct and extreme enough to be discernable by visual inspection. The changes in the PMO spectrophotometric characteristics upon exposure to different cyclic organic solvents can be noted by visual inspection. Quantitative analysis is possible using the red, green, blue color values obtained from the images. Idealized images were generated based on the red, green, and blue (RGB) color values for each of the images shown. Also shown are the difference images generated by the RGB subtraction of the ethanol only sample from the samples containing the various analytes. Each of the cyclic organics gives a unique set of RGB values and therefore a unique set of difference values.

Figure 7A:
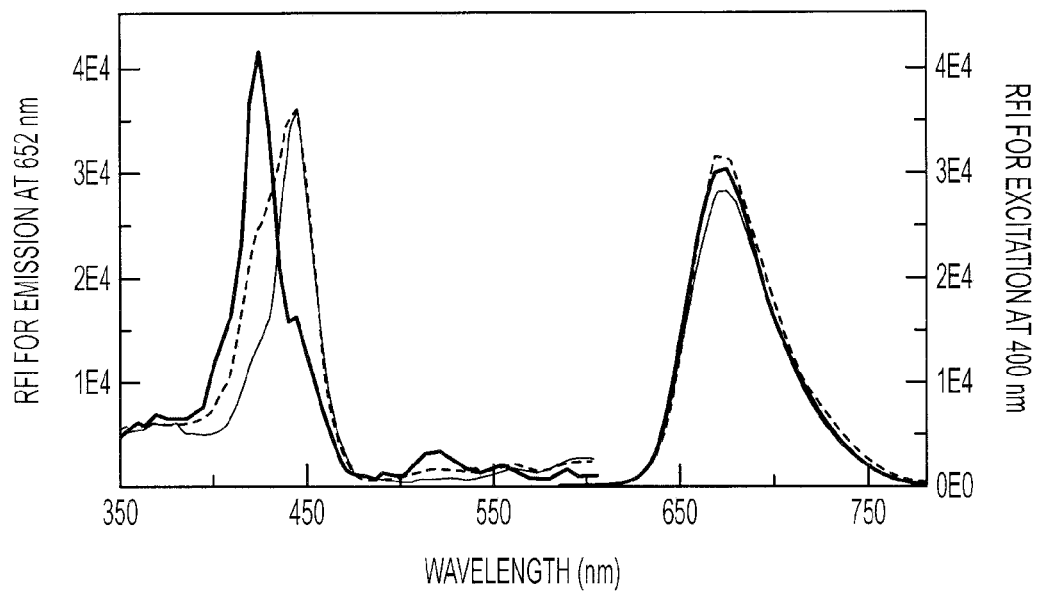
FIG. 7 shows fluorescence emission and excitation spectra for the materials.
Figure 7B:
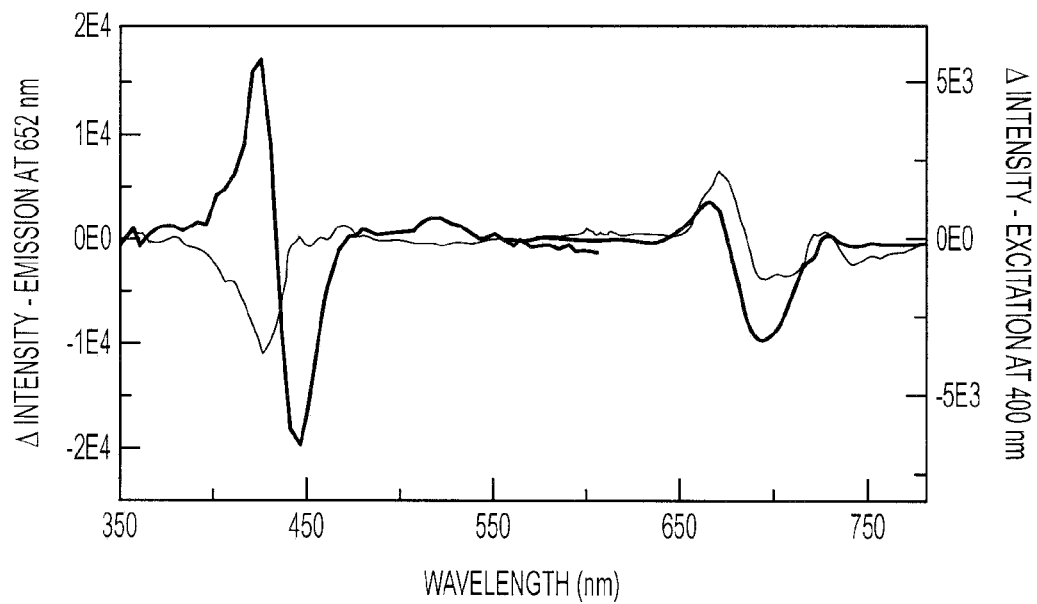
Figure 7C:
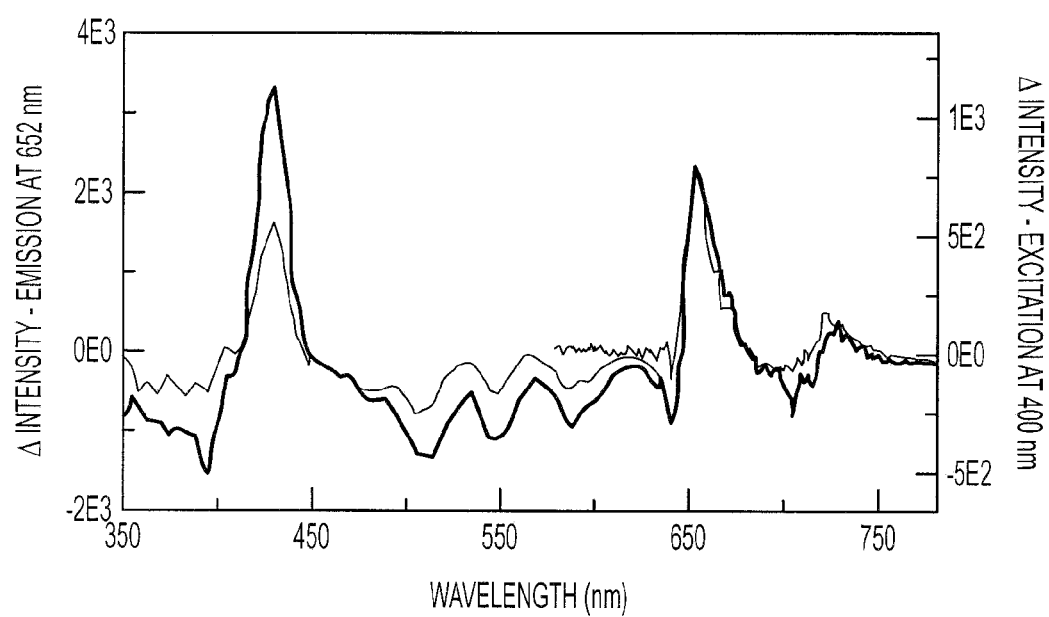

Fluorescence emission and excitation spectra for the materials used to collect each image are shown FIG. 7. Changes in both the excitation and emission spectra are unique (see FIG. 7(B) for each analyte though the changes in the emission spectra are similar with peak/trough pairs at 671/703 nm for cyclohexane and 665/695 nm for toluene. The changes in the excitation spectrum are more pronounced and distinct for each analyte with a trough only at 426 nm for cyclohexane and a peak/trough pair at 424/444 nm for toluene. FIG. 7(A) shows the unique fluorescence spectra of the PMO exposed to the three liquid phase samples presented in FIG. 6; ethanol ( - - - ), cyclohexane (■■■), and toluene (■■■). FIG. 7(B) shows the difference spectra calculated as PMO with sample minus PMO with ethanol emphasize the specific changes in the spectrum upon exposure to cyclohexane (■■■) and toluene (■■■) in solution. FIG. 7(C) shows the difference spectra calculated as PMO with sample minus PMO with ethanol emphasize the specific changes in the spectrum upon exposure to cyclohexane (■■■) and toluene (■■■) vapors.

The PMO material was also exposed to the volatile organic compounds as vapors. FIG. 6 shows the results from exposure of the powders to ethanol, cyclohexane, and toluene. Though the colors of the powders are less intense when dry, the changes upon exposure to each of the analytes are distinct and unique both via visual inspection and through the use of the RGB values as indicated in the idealized images. The fluorescence difference spectra (FIG. 7(C) can be used to emphasize the changes in the spectrophotometric characteristics of these materials upon exposure to the solvent vapors. Again, the changes in the fluorescence emission spectra are very similar for cyclohexane and toluene. The second derivatives of the difference spectra indicate the peak position is the same in both cases at 657 nm while the trough positions are at 699 nm and 708 nm for cyclohexane and toluene, respectively. The changes in the fluorescence excitation spectra are also similar but distinct with peaks at 432 nm and 429 nm and troughs at 376 nm and 383 nm, for cyclohexane and toluene, respectively.

Figure 8:
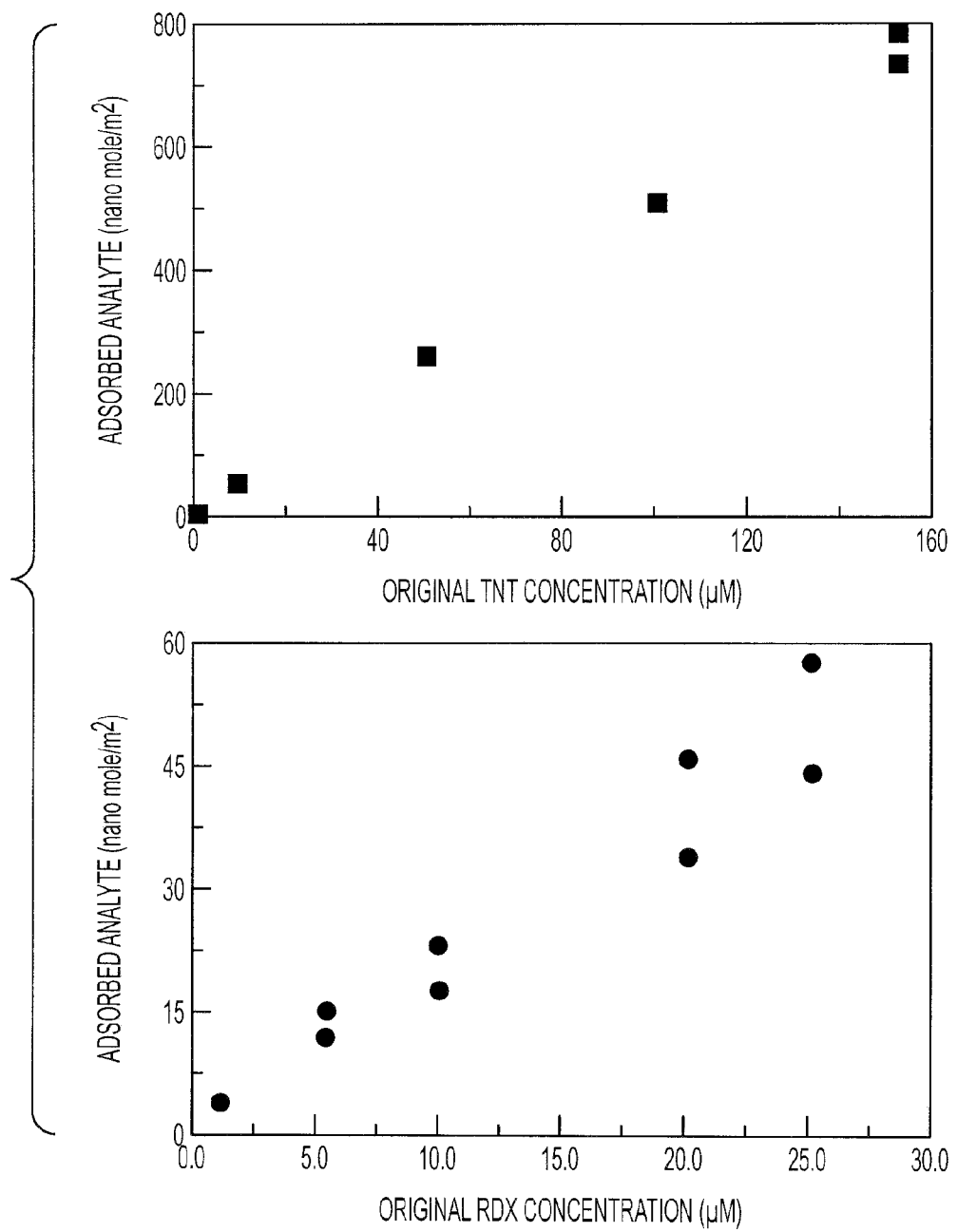
FIG. 8 shows the adsorption of TNT and RDX in nanomoles/$m^2$ by each of the materials

PMO detection of nitro-energetics and related compounds: The sensitivity and selectivity of porphyrin-embedded PMOs synthesized with (PMO-B) and without (PMO-A) template directed molecular imprinting to the presence of 2,4,6-trinitrotoluene, RDX, p-nitrophenol, and p-cresol were compared. Table 1 presents the results of HPLC analysis of analytes remaining in solution after equilibration with the different PMO materials. Both materials show a high degree of affinity for TNT adsorbing between 80% and 92% of TNT from solution when encountering it as the single present analyte. PMO-A adsorbs only 12.9% of p-nitrophenol, 43.4% of p-cresol, and 36.7% of RDX in single analyte solutions while PMO-B adsorbs 13.6% of p-nitrophenol, 35.9% of p-cresol, and 25.9% of RDX. When exposed to a ternary mixture of approximately equal concentrations of TNT, p-nitrophenol, and p-cresol, the higher degree of selectivity of PMO-B becomes more apparent where 31.8% of p-cresol, 82.1% of TNT, and just 0.6% of p-nitrophenol present in the solution was adsorbed as compared to 36.1% of p-cresol, 90.9% of TNT, and 22.0% of p-nitrophenol by PMO-A. The change in the binding affinity of the PMO upon imprinting can be seen through comparison of the percentages bound of TNT and RDX. For PMO-B, 80.5% of TNT is bound while only 25.9% of RDX is bound while in PMO-A 88.6% and 36.7% of TNT and RDX are bound, respectively. Though the binding affinity for TNT of both materials is higher than that for RDX, the material does not appear to selectively bind TNT over RDX as the percentages bound in a binary mixture reflect those observed in unitary solutions. The performance of both materials was approximately the same in aqueous solution or in artificial seawater. The specific surface area of PMO-A at 157 $m^2/g$ is slightly higher than that of PMO-B at 144 $m^2/g$. FIG. 8 shows the adsorption of TNT and RDX in nanomoles/m2 by each of the materials. FIG. 8 shows that both the imprinted (PMO-B) and non-imprinted PMO (PMO-A) materials show adsorption of TNT (FIG. 8(A)-PMO-A, ■; PMO-B, ●) and RDX (FIG. 8(B)-PMO-A, ■; PMO-B, ●), though with greater affinity for TNT. This data was obtained using HPLC difference method. PMO-A specific surface area=157 $m^2/g$; PMO-B specific surface area=144 $m^2/g$.

TABLE 1

| Material | Analyte | | Analyte (μM) | % adsorbed | Nanomole/m² adsorbed |
|---|---|---|---|---|---|
| Non-imprinted PMO-A | p-nitrophenol | | 49.2 | 12.9 | 40.8 |
| | p-cresol | | 51.7 | 43.4 | 143.3 |
| | 2,4,6-trinitrotoluene | | 54.1 | 91.2 | 312.7 |
| | Mixture #1 | p-nitrophenol | 50.1 | 22.0 | 70.1 |
| | | p-cresol | 50.4 | 36.1 | 115.9 |
| | | TNT | 52.1 | 90.9 | 301.9 |
| | 2,4,6-trinitrotoluene | | 9.9 | 88.6 | 56.7 |
| | RDX | | 10.0 | 36.7 | 23.6 |
| | Mixture #2 | TNT | 25.0 | 86.7 | 137.6 |
| | | RDX | 26.0 | 33.8 | 56.1 |
| | TNT in sea water | | 51.6 | 86.3 | 283.4 |
| | RDX in sea water | | 8.2 | 36.1 | 19.1 |
| Imprinted PMO-B | p-nitrophenol | | 49.2 | 13.6 | 46.5 |
| | p-cresol | | 51.7 | 35.9 | 128.4 |
| | 2,4,6-trinitrotoluene | | 54.1 | 91.2 | 312.5 |
| | Mixture #1 | p-nitrophenol | 50.1 | 0.6 | 2.1 |
| | | p-cresol | 50.4 | 31.8 | 111.1 |
| | | TNT | 52.1 | 82.1 | 297.2 |
| | 2,4,6-trinitrotoluene | | 9.9 | 80.5 | 55.6 |
| | RDX | | 10.0 | 25.9 | 18.1 |
| | Mixture #2 | TNT | 25.0 | 77.1 | 134 |
| | | RDX | 26.0 | 23.5 | 42.4 |
| | TNT in sea water | | 51.6 | 77.9 | 279.2 |
| | RDX in sea water | | 8.2 | 23.2 | 13.2 |

Figure 9A:
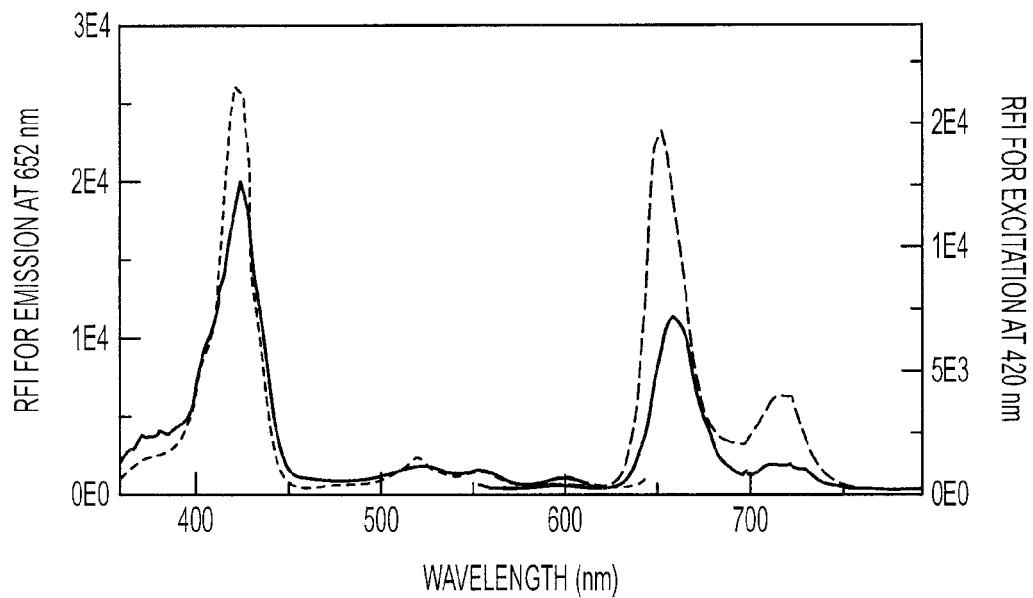
FIG. 9 shows the dependence on concentration of the changes in fluorescence intensity.
Figure 9B:
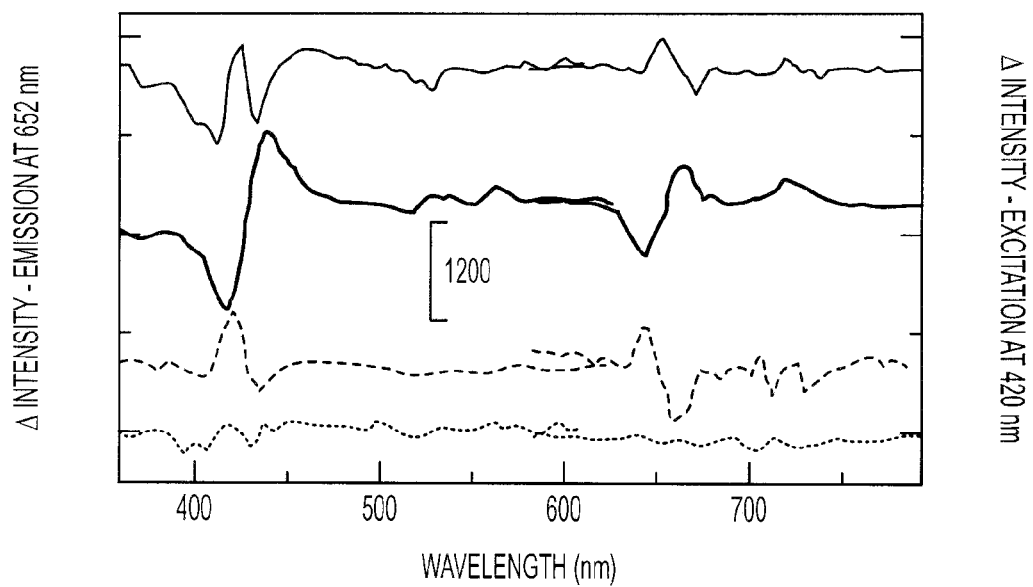
Figure 9C:
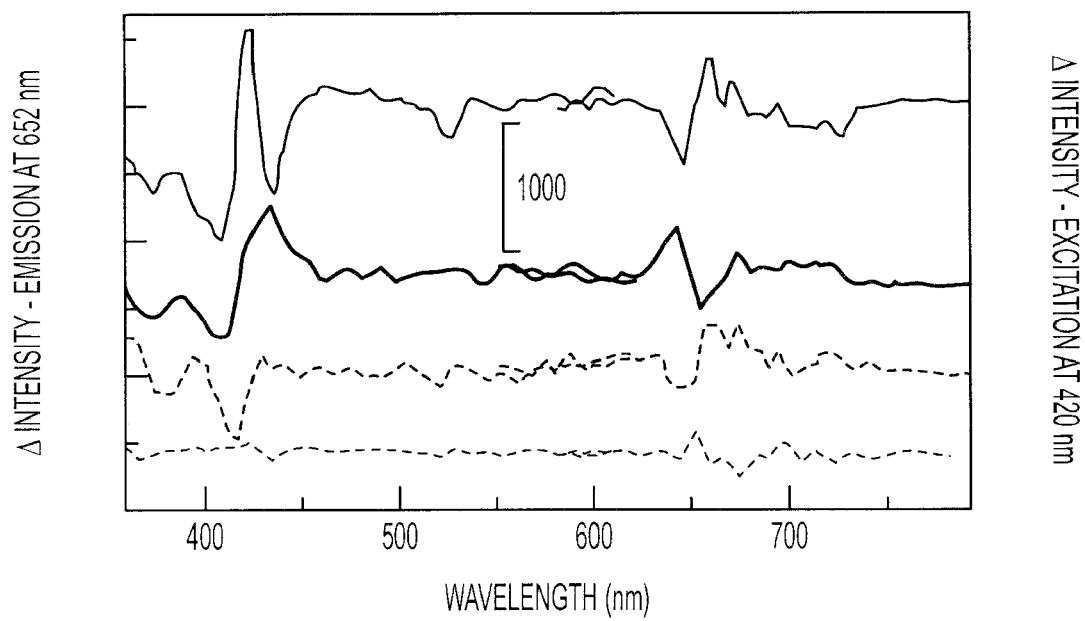

FIG. 9(A) shows the fluorescence excitation and emission characteristics of the non-imprinted PMO (PMO-A; - - -) are distinct from those of the porphyrin in solution and those of the imprinted PMO (PMO-B; ■■■). FIG. 9(B) shows the difference spectra PMO-A+analyte minus PMO-A for p-nitrophenol (■■■; 50 mM), TNT (■■■; 50 mM), RDX (- - -; 10 mM), and p-cresol (- - -; 50 mM) which shows the unique changes in the PMO-A spectra resulting from exposure to each analyte. FIG. 9(C) shows the difference spectra PMO-B+analyte minus PMO-B for p-nitrophenol (■■■; 50 mM), TNT (■■■; 50 mM), RDX (- - -; 10 mM), and p-cresol (- - -; 50 mM) which show the unique changes in the PMO-B spectra resulting from exposure to each analyte.

FIG. 9(A) shows the fluorescence excitation (at 660 nm emission) and emission (at 420 nm excitation) spectra for PMO-A. Though the excitation spectrum is very similar to the absorbance spectrum of the porphyrin in solution, the Soret peak of the porphyrin has shifted from 414 nm to 425 nm upon interaction with the PMO backbone and Q-bands are now observed at 523, 557, and 598 nm. The bands comprising the emission spectrum are more distinctly separated and the ratio of their intensities is different from that of the porphyrin in solution. The change in porphyrin spectrophotometric characteristics upon immobilization has been well documented (Awawdeh et al., *Solid-state optical detection of amino acids, Sensors and Actuators B-Chemical* 91, 227-230, 2003; Kibbey and Meyerhoff, *Preparation and characterization of covalently bound tetraphenylporphyrin-silica gel stationary phases for reversed-phase and anion-exchange chromatography, Analytical Chemistry* 65, 2189-2196, 1993; White and Harmon, *Interaction of dipicolinic acid with water-soluble and immobilized porphyrins, Sensors and Actuators B* 97, 277-83, 2004). The difference spectra presented in FIG. 9 (Panel B) show the changes in the spectrophotometric characteristics of PMO-A upon interaction with p-nitrophenol, TNT, RDX, and p-cresol. Changes in the emission spectra tend to be less intense than those of the excitation spectra. Exposure to p-cresol results in nearly no changes in the spectrophotometric characteristics of PMO-A. TNT and RDX exposure each result in unique difference spectra with peak/trough pairs at 440/417 nm and 421/436 nm, respectively, while exposure to p-nitrophenol results in a complex difference spectrum with several peaks and troughs.

FIG. 9(A) also presents the excitation and emission spectra for PMO-B material. The fluorescence excitation and emission characteristics for PMO-B are different from those of the porphyrin in solution and those of PMO-A. The PMO-B Soret peak is at 422 nm and is distinctly broadened as compared to that of both the porphyrin in solution and that of PMO-A. Q-bands are located at 521, 558, and 592 nm. The emission spectrum shows less separation of the emission bands than that observed for PMO-A and the bands are narrowed with an increase in the ratio of 655 nm to 721 nm emission. The difference spectrum resulting from exposure of PMO-B to p-cresol shows almost no changes in the spectrophotometric characteristics of the material (FIG. 9(C)). Exposure to p-nitrophenol yields a complicated excitation difference spectrum with features similar to those observed in the case of PMO-A exposure to p-nitrophenol. The emission difference spectra resulting from p-nitrophenol and RDX exposure have a nearly identical features while exposure to RDX results in an excitation difference spectrum with troughs but no peaks. The excitation and emission difference spectra resulting from the exposure of PMO-B to TNT are unique with a peak trough/pair at 433/410 nm in the excitation spectrum and at 643/656 nm in the emission spectrum.

Figure 10A:
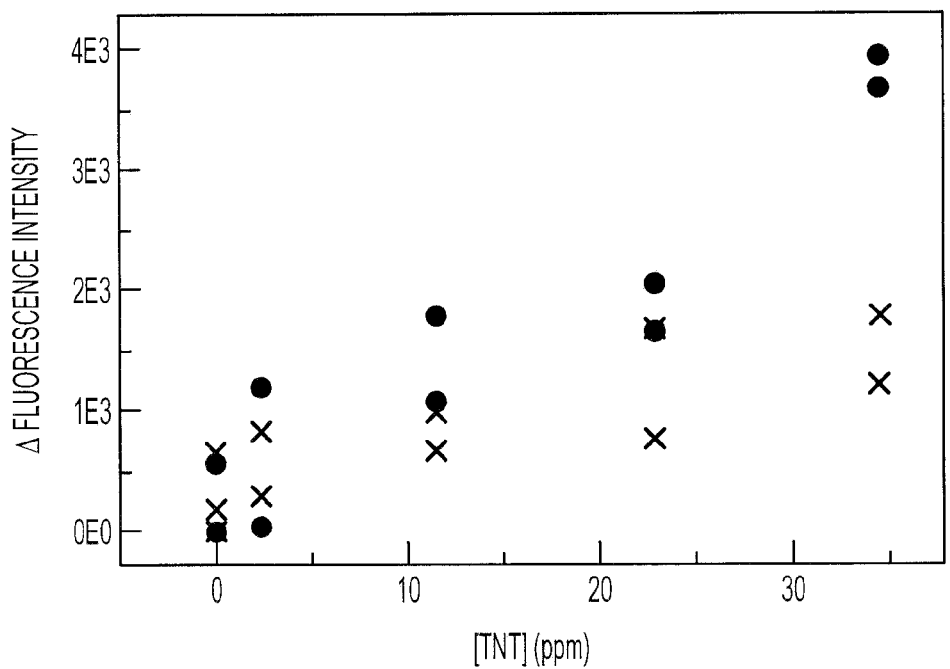
FIG. 10 shows the changes in the fluorescence excitation and emission spectra of the PMO materials are dependent on analyte concentration.
Figure 10B:
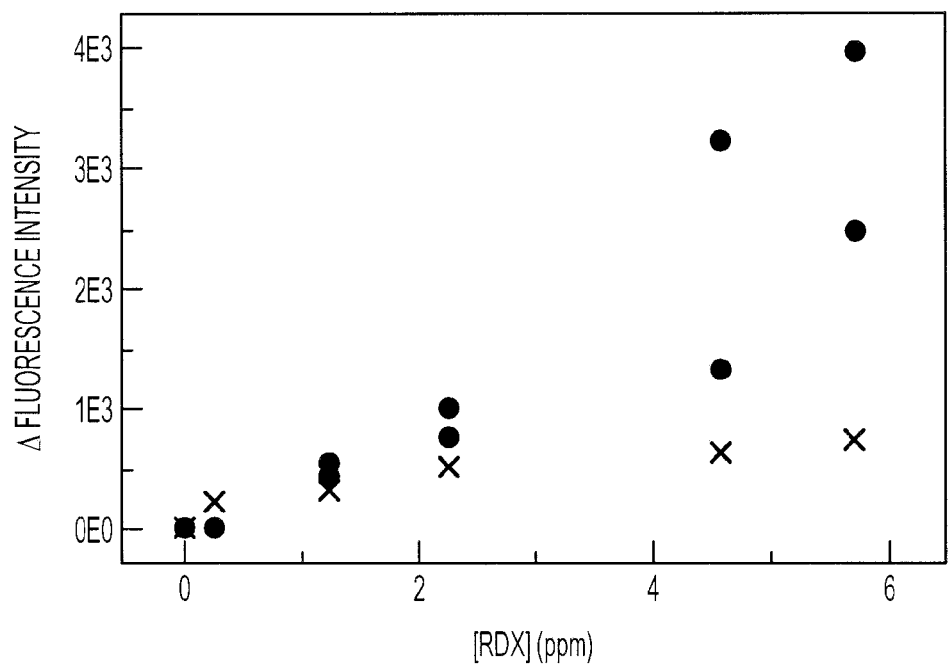

The dependence on concentration of the changes in fluorescence intensity described in FIG. 9 is presented in FIG. 10. FIG. 10 shows the changes in the fluorescence excitation (emission at 662 nm) and emission (excitation at 420 nm) spectra of the PMO materials are dependent on analyte concentration as shown here plotted as difference spectrum peak minus trough intensity. Two curves are presented for the intensity changes in the excitation spectrum (433 nm minus 410 nm=x) and the emission spectrum (643 nm minus 656 nm=x) of the imprinted PMO-B upon exposure to TNT (FIG. 10(A). Changes in emission only are presented for the interaction of PMO-B with RDX (666 nm minus 640 nm=x; Panel B). Changes in the fluorescence characteristics of the non-imprinted PMO-A are more intense than those observed for PMO-B. FIG. 10(A) presents the concentration dependence of the changes in excitation (440 nm minus 417 nm=●) and emission (663 nm minus 642 nm=●) upon exposure to TNT, while FIG. 10(B) presents the changes in excitation (421 nm minus 436 nm=●) and emission (645 nm minus 661 nm=●) upon exposure to RDX. Changes in excitation and emission spectra for PMO-A upon exposure to TNT follow similar trends. These changes are more intense than the trends observed for PMO-B upon exposure to TNT. The dependence on concentration of the changes in PMO-A and PMO-B spectra do not follow one of the simple binding models (Connors, *Binding Constants: The Measurement of Molecular Complex Stability*, John Wiley & Sons, New York, 1987; White and Harmon, *Sensors and Actuators B* 97, 277-83, 2004). Exposure of PMO-B materials to TNT and RDX in artificial seawater resulted in changes in the fluorescence excitation and emission spectra identical to those resulting from exposure to the analytes in deionized water with the exception that the intensities were reduced by approximately 30% for TNT and 50% for RDX. Exposure of PMO-A material to TNT and RDX in artificial sea water resulted in no detectable changes in the excitation or emission characteristics of the porphyrin-embedded material.

Immobilizing the porphyrin in the PMO matrix results in changes in fluorescence characteristics which are expected based on previously published work (Awawdeh et al., *Sensors and Actuators B-Chemical* 91, 227-230, 2003; Kibbey and Meyerhoff, *Preparation and characterization of covalently bound tetraphenylporphyrin-silica gel stationary phases for reversed-phase and anion-exchange chromatography*, 1993; White and Harmon, *Sensors and Actuators B* 97, 277-83, 2004). Reflectance and fluorescence experiments indicate a lower concentration of porphyrin per square meter in the imprinted PMO (PMO-B) as compared to the non-imprinted PMO (PMO-A). This is reflected in the lower intensity of the changes in PMO-B spectrophotometric characteristics upon exposure to the various analytes as the intensity of the changes in the porphyrin spectrum are dependent on both analyte concentration and porphyrin concentration (White and Harmon, *Optical Determination of Bacterial Exosporium Sugars Using Immobilized Porphyrins, IEEE Sensors Journal* 5, 726-732, 2005).

The concentration dependence of the changes in the fluorescence spectra are complicated. Linearization of the data can not be accomplished using a double reciprocal plot making generation of a binding model a complex task. The concentration dependence curve for PMO-A is similar to curves observed for cooperative binding. While cooperativity is possible, it is more likely that there exist various different types of binding sites each with a different binding affinity that together result in this complicated trend. At first glance, the concentration dependence for PMO-B appears to be half-hyperbolic. This is, unfortunately, not the case. PMO-B has a highly homogenous distribution of binding sites, however, there is no guarantee that the bound porphyrin is interacting with each site identically, that all porphyrins are equally accessible, or that there is a porphyrin available at all binding sites. In fact, it is more likely that various porphyrin-binding site interactions take place, porphyrins are present in a wide range of locations with varying accessibility, and most binding sites are not associated with a porphyrin. Each of these points would contribute to a complicated binding model.

The higher selectivity of binding of PMO-B and the reduced sensitivity to the sample matrix are points of note. PMO-A gave higher intensity changes upon exposure to the various analytes using this porphyrin, however, the selectivity of PMO-B eliminates the contribution of the p-nitrophenol in complex samples. The result is that for PMO-A in the presence of a mixed sample you get a complex difference spectrum that must be deconvoluted to yield information on the encountered analytes. PMO-B, on the other hand, yields the difference spectrum expected for TNT exposure when exposed to a mixed sample of TNT, p-nitrophenol, and p-cresol.

The materials described here could provide some advantages over the techniques currently in use. It has been reported that 96% of target analytes can be absorbed by PMOs in the first minute of contact with 99% adsorbed within 15 minutes (Burleigh et al., 2002). These time frames are slightly longer than those quoted for ion mobility and electron capture spectroscopy, which require only seconds. Detection times are similar to those possible with surface acoustic wave, semiconducting organic polymer, and amplifying fluorescent polymer detection. The materials described have the potential for discrimination between molecules of similar structure such as TNT, RDX, and p-nitrophenol. Methods using semiconducting polymer, surface acoustic wave, ion mobility, or electron capture detection are subject to false signals resulting from analytes of similar structure, similar mass, or those possessing similar drift times to the targets. The materials described also provide the potential for quantitative analysis and should be functional within a complex sample due to the preferential binding of surfaces to target analytes. Though the sensitivities reported for amplifying fluorescent polymer detection are lower than those reported here, that technique relies solely on quenching of the fluorescence signal. The materials described here employ a pair of wavelengths for which one displays a decrease in intensity while the other displays an increase in intensity upon analyte interaction. This additional information should reduce the potential for false positive signals as non-analyte induced quenching is an insufficient indicator of analyte presence.

Porphyrin-embedded periodic mesoporous materials to be used for the detection of volatile organic compounds (VOCs) using simple methods of interrogation not requiring lasers or highly sensitive spectrophotometric equipment are disclosed. Additionally, template directed molecular imprinting can be used during the synthesis of the porphyrin-embedded PMO to obtain a higher degree of selectivity as evidenced by adsorption studies.

Materials like the porphyrin-embedded periodic mesoporous organosilicas described here could be applied in a range of optical detection schemes similar to those used with antibodies, enzymes, or dye molecules. The experiments presented here indicate that porphyrin-embedded PMO materials have the potential to provide detection capabilities competitive with those currently in use, addressing the issue of false positives while requiring slightly longer for detection. The materials could be used as disposable recognition and transduction elements with miniaturized spectrophotometers for hand-held instruments or remote detection using WiFi. Another possibility for materials of this type is the application of a layer to a surface found in area where monitoring would be of interest. The material could potentially be interrogated from a distance using laser-based reflectance spectroscopy.

Obviously, many modifications and variations of the present invention are possible in light of the above teachings. It is therefore to be understood that, within the scope of the appended claims, the invention may be practiced otherwise than as specifically described.

What is claimed as new and desired to be protected by Letters Patent of the United States is:

1. A method for detecting a target molecule in a sample comprising:
    providing a periodic mesoporous organosilica incorporating an optically active molecule, wherein said periodic mesoporous organosilica is configured to orient a target molecule with respect to said optically active molecule;
    providing a sample containing a target molecule;
    exposing said periodic mesoporous organosilica to said sample, wherein said target molecule is adsorbed into said periodic mesoporous organosilica;
    providing a light source; and
    exposing said periodic mesoporous organosilica to said light source, wherein said optically active molecule undergoes a change that detects the presence of said target molecule.

2. The method of claim 1 wherein said optically active molecule is a fluorophore or chromophore.

3. The method of claim 1 wherein said optically active molecule is selected from the group consisting of porphyrins and phthalocyanines.

4. The method of claim 2 wherein said chromophore or fluorophore is selected from fluorescein and fluorescein derivatives and analogues, indocyanine green, rhodamine, triphenylmethines, polymethines, cyanines, phalocyanines, naphthocyanines, merocyanines, lanthanide complexes or cryptates, fullerenes, oxatellurazoles, LaJolla blue, porphyrins and porphyrin analogues and natural chromophores/fluorophores such as chlorophyll, carotenoids, flavonoids, bilins, phytochrome, phycobilins, phycoerythrin, phycocyanines, retinoic acid and analogues such as retinoins and retinates.

5. The method of claim 1 wherein said periodic mesoporous organosilica is a molecularly imprinted periodic mesoporous organosilica.

6. The method of claim 5 wherein said periodic mesoporous organosilica is a template directed molecularly imprinted periodic mesoporous organosilica.

7. The method of claim 1 wherein the target molecule is TNT, TNT-derivatives, chemical warfare agents, pesticides, or volatile organic compounds.

8. The method of claim 1 wherein said light source covers the blue to red regions of the visible spectrum.

9. The method of claim 8 wherein said light source is sunlight.

10. A system for detecting a target molecule in a sample comprising:
   a periodic mesoporous organosilica incorporating an optically active molecule, said optically active molecule, wherein said periodic mesoporous organosilica is configured to orient a target molecule with respect to said optically active molecule;
   means for exposing said periodic mesoporous organosilica to a sample containing a target molecule, wherein said optically active molecule undergoes a change in the presence of said target molecule; and
   a means for visualizing said change in said optically active molecule, said change indicating the presence of said target molecule in said sample.

11. The system of claim 10 wherein said optically active molecule is a fluorophore or chromophore.

12. The system of claim 10 wherein said optically active molecule is selected from the group consisting of porphyrins and phthalocyanines.

13. The system of claim 11 wherein said chromophore or fluorophore is selected from fluorescein and fluorescein derivatives and analogues, indocyanine green, rhodamine, triphenylmethines, polymethines, cyanines, phalocyanines, naphthocyanines, merocyanines, lanthanide complexes or cryptates, fullerenes, oxatellurazoles, LaJolla blue, porphyrins and porphyrin analogues and natural chromophores/fluorophores such as chlorophyll, carotenoids, flavonoids, bilins, phytochrome, phycobilins, phycoerythrin, phycocyanines, retinoic acid and analogues such as retinoins and retinates.

14. The system of claim 10 wherein said periodic mesoporous organosilica is a molecularly imprinted periodic mesoporous organosilica.

15. The system of claim 14 wherein said periodic mesoporous organosilica is a template directed molecularly imprinted periodic mesoporous organosilica.

16. The system of claim 10 wherein the target molecule is TNT, TNT-derivatives, chemical warfare agents, pesticides, or volatile organic compounds.

17. The system of claim 10 wherein said light source covers the blue to red regions of the visible spectrum.

18. The system of claim 17 wherein said light source is sunlight.

* * * * *